United States Patent [19]

MacKellar

[11] Patent Number: 5,614,379
[45] Date of Patent: Mar. 25, 1997

[54] PROCESS FOR PREPARING ANTI-OBESITY PROTEIN

[75] Inventor: Warren C. MacKellar, Plainfield, Ind.

[73] Assignee: Eli Lilly and Company, Indianapolis, Ind.

[21] Appl. No.: 429,362

[22] Filed: Apr. 26, 1995

[51] Int. Cl.$^6$ ................................................. C12P 21/02
[52] U.S. Cl. ........................................ 435/68.1; 435/212
[58] Field of Search .................................. 435/68.1, 212

[56] References Cited

U.S. PATENT DOCUMENTS 5,126,249  6/1992  Becker et al. ........................ 435/68.1

FOREIGN PATENT DOCUMENTS

| 0397420 | 5/1990 | European Pat. Off. ........ C12P 21/00 |
| 0217814 | 5/1990 | European Pat. Off. ........ C12P 21/06 |
| 659886 | 6/1995 | European Pat. Off. . |
| WO96/05309 | 2/1996 | WIPO . |

OTHER PUBLICATIONS

Zhang, et al., "Positional cloning of the mouse obese gene and its human homologue", *Nature*, 372:1, 425–432 (Dec. 1, 1994).

Rink, "In search of a satiety factor", *Nature*, 372:1, 406–407 (Dec. 1, 1994).

Flam, "Obesity Gene Discovery May Help Solve Weighty Problem", *Science*, 266, 1477–1478 (Dec. 2, 1994).

Chan, et al., "Dipeptidyl–Aminopeptidases and Aminopeptidases in *Dictyostelium discoideum*", *Biochemical and Biophysical Research Communications*, 127:3, 962–968 (Mar. 29, 1985).

Chan, et al., "Partial Purification and Characterization of Dipeptidyl–aminopeptidase III from *Dictyostelium discoideum*", *Experimental Mycology*, 11, 27–35 (1987).

Hutchinson, et al., "The preparation and properties of immobilised dipeptidyl–aminopeptidase I (cathepsin C)", *Biochimica et Biophysica Acta*, 916, 1–4 (1987).

Erickson, et al., "Interaction of Purified Brush Border Membrane Aminopeptidase N and Dipeptidyl Peptidase IV with Lectin–Sepharose Derivatives", *Biochimica et Biophysica Acta*, 743, 37–42 (1983).

Huang, et al. "The Purification, Specificity, and Role of Dipeptidyl Peptidase III in *Dictyostelium discoideum*", *Experimental Mycology*, 16, 102–109 (1992).

Primary Examiner—Herbert J. Lilling
Attorney, Agent, or Firm—Steven P. Caltrider; David E. Boone

[57] ABSTRACT

The present invention is directed to a novel process of preparing an anti-obesity protein using dipeptidyl-aminopeptidase isolated from the cellular slime mold, *Dictyostelium discodeum*. The process produces an anti-obesity protein in high yield.

10 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 146 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Modified-site
( B ) LOCATION: 4
( D ) OTHER INFORMATION: /note= "Xaa at position 4 is Gln
or Glu;"

( i x ) FEATURE:
( A ) NAME/KEY: Modified-site
( B ) LOCATION: 7
( D ) OTHER INFORMATION: /note= "Xaa at position 7 is Gln
or Glu;"

( i x ) FEATURE:
( A ) NAME/KEY: Modified-site
( B ) LOCATION: 22
( D ) OTHER INFORMATION: /note= "Xaa at position 22 is Gln,
Asn or Asp;"

( i x ) FEATURE:
( A ) NAME/KEY: Modified-site
( B ) LOCATION: 27
( D ) OTHER INFORMATION: /note= "Xaa at position 27 is Thr
or Ala;"

( i x ) FEATURE:
( A ) NAME/KEY: Modified-site
( B ) LOCATION: 28
( D ) OTHER INFORMATION: /note= "Xaa at position 28 is Gln,
Glu, or absent;"

( i x ) FEATURE:
( A ) NAME/KEY: Modified-site
( B ) LOCATION: 34
( D ) OTHER INFORMATION: /note= "Xaa at position 34 is Gln
or Glu;"

( i x ) FEATURE:
( A ) NAME/KEY: Modified-site
( B ) LOCATION: 54
( D ) OTHER INFORMATION: /note= "Xaa at position 54 is Met,
methionine sulfoxide, Leu, Ile, Val, Ala, or Gly;"

( i x ) FEATURE:
( A ) NAME/KEY: Modified-site
( B ) LOCATION: 56
( D ) OTHER INFORMATION: /note= "Xaa at position 56 is Gln
or Glu;"

( i x ) FEATURE:
( A ) NAME/KEY: Modified-site
( B ) LOCATION: 62
( D ) OTHER INFORMATION: /note= "Xaa at position 62 is Gln
or Glu;"

( i x ) FEATURE:
( A ) NAME/KEY: Modified-site
( B ) LOCATION: 63
( D ) OTHER INFORMATION: /note= "Xaa at position 63 is Gln
or Glu;;"

( i x ) FEATURE:
( A ) NAME/KEY: Modified-site (B) LOCATION: 68
(D) OTHER INFORMATION: /note= "Xaa at position 68 is Met, methionine sulfoxide, Leu, Ile, Val, Ala, or Gly;"

(ix) FEATURE:
(A) NAME/KEY: Modified-site
(B) LOCATION: 72
(D) OTHER INFORMATION: /note= "Xaa at position 72 is Gln, Asn, or Asp;"

(ix) FEATURE:
(A) NAME/KEY: Modified-site
(B) LOCATION: 75
(D) OTHER INFORMATION: /note= "Xaa at position 75 is Gln or Glu;"

(ix) FEATURE:
(A) NAME/KEY: Modified-site
(B) LOCATION: 78
(D) OTHER INFORMATION: /note= "Xaa at position 78 is Gln, Asn or Asp;"

(ix) FEATURE:
(A) NAME/KEY: Modified-site
(B) LOCATION: 82
(D) OTHER INFORMATION: /note= "Xaa at position 82 is Gln, Asn, or Asp;"

(ix) FEATURE:
(A) NAME/KEY: Modified-site
(B) LOCATION: 100
(D) OTHER INFORMATION: /note= "Xaa at position 100 is Gln, Trp, Tyr, Phe, Ile, Val, or Leu;"

(ix) FEATURE:
(A) NAME/KEY: Modified-site
(B) LOCATION: 108
(D) OTHER INFORMATION: /note= "Xaa at position 108 is Asp or Glu;"

(ix) FEATURE:
(A) NAME/KEY: Modified-site
(B) LOCATION: 130
(D) OTHER INFORMATION: /note= "Xaa at position 130 is Gln or Glu;"

(ix) FEATURE:
(A) NAME/KEY: Modified-site
(B) LOCATION: 134
(D) OTHER INFORMATION: /note= "Xaa at position 134 is Gln or Glu;"

(ix) FEATURE:
(A) NAME/KEY: Modified-site
(B) LOCATION: 136
(D) OTHER INFORMATION: /note= "Xaa at position 136 is Met, methionine sulfoxide, Leu, Ile, Val, Ala, or Gly;"

(ix) FEATURE:
(A) NAME/KEY: Modified-site
(B) LOCATION: 138
(D) OTHER INFORMATION: /note= "Xaa at position 138 is Gln, Trp, Tyr, Phe, Ile, Val, or Leu;"

(ix) FEATURE:
(A) NAME/KEY: Modified-site
(B) LOCATION: 139
(D) OTHER INFORMATION: /note= "Xaa at position 139 is Gln or Glu."

(xi) SEQUENCE DESCRIPTION: SEQ ID NO:1:

```
Val Pro Ile Xaa Lys Val Xaa Asp Asp Thr Lys Thr Leu Ile Lys Thr
 1               5                  10                  15
Ile Val Thr Arg Ile Xaa Asp Ile Ser His Xaa Xaa Ser Val Ser Ser
```

```
                         20                          25                          30
Lys  Xaa  Lys  Val  Thr  Gly  Leu  Asp  Phe  Ile  Pro  Gly  Leu  His  Pro  Ile
     35                           40                      45

Leu  Thr  Leu  Ser  Lys  Xaa  Asp  Xaa  Thr  Leu  Ala  Val  Tyr  Xaa  Xaa  Ile
     50                      55                      60

Leu  Thr  Ser  Xaa  Pro  Ser  Arg  Xaa  Val  Ile  Xaa  Ile  Ser  Xaa  Asp  Leu
65                  70                           75                           80

Glu  Xaa  Leu  Arg  Asp  Leu  Leu  His  Val  Leu  Ala  Phe  Ser  Lys  Ser  Cys
               85                           90                      95

His  Leu  Pro  Xaa  Ala  Ser  Gly  Leu  Glu  Thr  Leu  Xaa  Ser  Leu  Gly  Gly
               100                      105                     110

Val  Leu  Glu  Ala  Ser  Gly  Tyr  Ser  Thr  Glu  Val  Val  Ala  Leu  Ser  Arg
          115                      120                     125

Leu  Xaa  Gly  Ser  Leu  Xaa  Asp  Xaa  Leu  Xaa  Xaa  Leu  Asp  Leu  Ser  Pro
     130                 135                     140

Gly  Cys
145
```

(2) INFORMATION FOR SEQ ID NO:2:

(i) SEQUENCE CHARACTERISTICS:
        (A) LENGTH: 148 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Modified-site
        (B) LOCATION: 2
        (D) OTHER INFORMATION: /note= "Xaa at position 2 is any amino acid except Pro;"

(ix) FEATURE:
        (A) NAME/KEY: Modified-site
        (B) LOCATION: 6
        (D) OTHER INFORMATION: /note= "Xaa at position 6 is Gln or Glu;"

(ix) FEATURE:
        (A) NAME/KEY: Modified-site
        (B) LOCATION: 9
        (D) OTHER INFORMATION: /note= "Xaa at position 9 is Gln or Glu;"

(ix) FEATURE:
        (A) NAME/KEY: Modified-site
        (B) LOCATION: 24
        (D) OTHER INFORMATION: /note= "Xaa at position 24 is Gln, Asn or Asp;"

(ix) FEATURE:
        (A) NAME/KEY: Modified-site
        (B) LOCATION: 29
        (D) OTHER INFORMATION: /note= "Xaa at position 29 is Thr or Ala;"

(ix) FEATURE:
        (A) NAME/KEY: Modified-site
        (B) LOCATION: 30
        (D) OTHER INFORMATION: /note= "Xaa at position 30 is Gln, Glu, or absent;"

(ix) FEATURE:
        (A) NAME/KEY: Modified-site
        (B) LOCATION: 36
        (D) OTHER INFORMATION: /note= "Xaa at position 36 is Gln or Glu;"

(ix) FEATURE:

```
                ( A ) NAME/KEY: Modified-site
                ( B ) LOCATION: 56
                ( D ) OTHER INFORMATION: /note= "Xaa at position 56 is Met,
                        methionine sulfoxide, Leu, Ile, Val, Ala, or Gly;"

( i x ) FEATURE:
                ( A ) NAME/KEY: Modified-site
                ( B ) LOCATION: 58
                ( D ) OTHER INFORMATION: /note= "Xaa at position 58 is Gln
                        or Glu;"

( i x ) FEATURE:
                ( A ) NAME/KEY: Modified-site
                ( B ) LOCATION: 64
                ( D ) OTHER INFORMATION: /note= "Xaa at position 64 is Gln
                        or Glu;"

( i x ) FEATURE:
                ( A ) NAME/KEY: Modified-site
                ( B ) LOCATION: 65
                ( D ) OTHER INFORMATION: /note= "Xaa at position 65 is Gln
                        or Glu;"

( i x ) FEATURE:
                ( A ) NAME/KEY: Modified-site
                ( B ) LOCATION: 70
                ( D ) OTHER INFORMATION: /note= "Xaa at position 70 is Met,
                        methionine sulfoxide, Leu, Ile, Val, Ala, or Gly"

( i x ) FEATURE:
                ( A ) NAME/KEY: Modified-site
                ( B ) LOCATION: 74
                ( D ) OTHER INFORMATION: /note= "Xaa at position 74 is Gln,
                        Asn, or Asp;"

( i x ) FEATURE:
                ( A ) NAME/KEY: Modified-site
                ( B ) LOCATION: 77
                ( D ) OTHER INFORMATION: /note= "Xaa at position 77 is Gln
                        or Glu;"

( i x ) FEATURE:
                ( A ) NAME/KEY: Modified-site
                ( B ) LOCATION: 80
                ( D ) OTHER INFORMATION: /note= "Xaa at position 80 is Gln,
                        Asn, or Asp;"

( i x ) FEATURE:
                ( A ) NAME/KEY: Modified-site
                ( B ) LOCATION: 84
                ( D ) OTHER INFORMATION: /note= "Xaa at position 84 is Gln,
                        Asn, or Asp;"

( i x ) FEATURE:
                ( A ) NAME/KEY: Modified-site
                ( B ) LOCATION: 102
                ( D ) OTHER INFORMATION: /note= "Xaa at position 102 is
                        Gln,
                        Trp, Tyr, Phe, Ile, Val, or Leu;"

( i x ) FEATURE:
                ( A ) NAME/KEY: Modified-site
                ( B ) LOCATION: 110
                ( D ) OTHER INFORMATION: /note= "Xaa at position 110 is Asp
                        or Glu;"

( i x ) FEATURE:
                ( A ) NAME/KEY: Modified-site
                ( B ) LOCATION: 132
                ( D ) OTHER INFORMATION: /note= "Xaa at position 132 is Gln
                        or Glu;"

( i x ) FEATURE:
                ( A ) NAME/KEY: Modified-site
                ( B ) LOCATION: 136
                ( D ) OTHER INFORMATION: /note= "Xaa at position 136 is Gln
                        or Glu;"

( i x ) FEATURE:
                ( A ) NAME/KEY: Modified-site
```

(B) LOCATION: 138
(D) OTHER INFORMATION: /note= "Xaa at position 138 is Met, methionine sulfoxide, Leu, Ile, Val, Ala, or Gly;"

(ix) FEATURE:
(A) NAME/KEY: Modified-site
(B) LOCATION: 140
(D) OTHER INFORMATION: /note= "Xaa at position 140 is Gln, Trp, Tyr, Phe, Ile, Val, or Leu;"

(ix) FEATURE:
(A) NAME/KEY: Modified-site
(B) LOCATION: 141
(D) OTHER INFORMATION: /note= "Xaa at position 141 is Gln or Glu."

(xi) SEQUENCE DESCRIPTION: SEQ ID NO:2:

| Met | Xaa | Val | Pro | Ile | Xaa | Lys | Val | Xaa | Asp | Asp | Thr | Lys | Thr | Leu | Ile |
|---|---|---|---|---|---|---|---|---|---|---|---|---|---|---|---|
| 1 | | | | 5 | | | | | 10 | | | | | 15 | |
| Lys | Thr | Ile | Val | Thr | Arg | Ile | Xaa | Asp | Ile | Ser | His | Xaa | Xaa | Ser | Val |
| | | | 20 | | | | 25 | | | | | 30 | | | |
| Ser | Ser | Lys | Xaa | Lys | Val | Thr | Gly | Leu | Asp | Phe | Ile | Pro | Gly | Leu | His |
| | | 35 | | | | | 40 | | | | | 45 | | | |
| Pro | Ile | Leu | Thr | Leu | Ser | Lys | Xaa | Asp | Xaa | Thr | Leu | Ala | Val | Tyr | Xaa |
| | 50 | | | | | 55 | | | | | 60 | | | | |
| Xaa | Ile | Leu | Thr | Ser | Xaa | Pro | Ser | Arg | Xaa | Val | Ile | Xaa | Ile | Ser | Xaa |
| 65 | | | | | 70 | | | | | 75 | | | | | 80 |
| Asp | Leu | Glu | Xaa | Leu | Arg | Asp | Leu | Leu | His | Val | Leu | Ala | Phe | Ser | Lys |
| | | | | 85 | | | | | 90 | | | | | 95 | |
| Ser | Cys | His | Leu | Pro | Xaa | Ala | Ser | Gly | Leu | Glu | Thr | Leu | Xaa | Ser | Leu |
| | | | 100 | | | | | 105 | | | | | 110 | | |
| Gly | Gly | Val | Leu | Glu | Ala | Ser | Gly | Tyr | Ser | Thr | Glu | Val | Val | Ala | Leu |
| | | 115 | | | | | 120 | | | | | 125 | | | |
| Ser | Arg | Leu | Xaa | Gly | Ser | Leu | Xaa | Asp | Xaa | Leu | Xaa | Xaa | Leu | Asp | Leu |
| | 130 | | | | | 135 | | | | | 140 | | | | |
| Ser | Pro | Gly | Cys | | | | | | | | | | | | |
| 145 | | | | | | | | | | | | | | | |

(2) INFORMATION FOR SEQ ID NO:3:

(i) SEQUENCE CHARACTERISTICS:
(A) LENGTH: 148 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:3:

| Met | Arg | Val | Pro | Ile | Gln | Lys | Val | Gln | Asp | Asp | Thr | Lys | Thr | Leu | Ile |
|---|---|---|---|---|---|---|---|---|---|---|---|---|---|---|---|
| 1 | | | | 5 | | | | | 10 | | | | | 15 | |
| Lys | Thr | Ile | Val | Thr | Arg | Ile | Asn | Asp | Ile | Ser | His | Thr | Gln | Ser | Val |
| | | | 20 | | | | 25 | | | | | 30 | | | |
| Ser | Ser | Lys | Gln | Lys | Val | Thr | Gly | Leu | Asp | Phe | Ile | Pro | Gly | Leu | His |
| | | 35 | | | | | 40 | | | | | 45 | | | |
| Pro | Ile | Leu | Thr | Leu | Ser | Lys | Met | Asp | Gln | Thr | Leu | Ala | Val | Tyr | Gln |
| | 50 | | | | | 55 | | | | | 60 | | | | |
| Gln | Ile | Leu | Thr | Ser | Met | Pro | Ser | Arg | Asn | Val | Ile | Gln | Ile | Ser | Asn |
| 65 | | | | | 70 | | | | | 75 | | | | | 80 |
| Asp | Leu | Glu | Asn | Leu | Arg | Asp | Leu | Leu | His | Val | Leu | Ala | Phe | Ser | Lys |
| | | | | 85 | | | | | 90 | | | | | 95 | |

```
Ser Cys His Leu Pro Trp Ala Ser Gly Leu Glu Thr Leu Asp Ser Leu
            100                 105                 110

Gly Gly Val Leu Glu Ala Ser Gly Tyr Ser Thr Glu Val Val Ala Leu
            115                 120                 125

Ser Arg Leu Gln Gly Ser Leu Gln Asp Met Leu Trp Gln Leu Asp Leu
    130                 135                 140

Ser Pro Gly Cys
145
```

( 2 ) INFORMATION FOR SEQ ID NO:4:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

GGGGCATATG AGGGTACCTA TCCAGAAAGT CCAGGATGAC AC    42

( 2 ) INFORMATION FOR SEQ ID NO:5:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

GGGGGGATCC TATTAGCACC CGGGAGACAG GTCCAGCTGC CACAACAT    48

PROCESS FOR PREPARING ANTI-OBESITY PROTEIN

FIELD OF THE INVENTION

This invention is in the field of biotechnology. More specifically, this invention concerns a process for preparing an anti-obesity protein of SEQ ID NO: 1 using dipeptidyl-aminopeptidase isolated from the slime mold, Dictyostelium discoideum.

BACKGROUND OF THE INVENTION

Obesity, and especially upper body obesity, is a common and very serious public health problem in the United States and throughout the world. According to recent statistics, more than 25% of the United States population and 27% of the Canadian population are over weight. Kuczmarski, Amer. J. of Clin. Nut. 55: 495S–502S (1992); Reeder et. al., Can. Med. Ass. J., 23:226–233 (1992). Upper body obesity is the strongest risk factor known for type II diabetes mellitus, and is a strong risk factor for cardiovascular disease and cancer as well. Recent estimates for the medical cost of obesity are $150,000,000,000 world wide. The problem has become serious enough that the surgeon general has begun an initiative to combat the ever increasing adiposity rampant in American society.

Much of this obesity induced pathology can be attributed to the strong association with dyslipidemia, hypertension, and insulin resistance. Many studies have demonstrated that reduction in obesity by diet and exercise reduces these risk factors dramatically. Unfortunately, these treatments are largely unsuccessful with a failure rate reaching 95%. This failure may be due to the fact that the condition is strongly associated with genetically inherited factors that contribute to increased appetite, preference for highly caloric foods, reduced physical activity, and increased lipogenic metabolism. This indicates that people inheriting these genetic traits are prone to becoming obese regardless of their efforts to combat the condition. Therefore, a pharmacological agent that can correct this adiposity handicap and allow the physician to successfully treat obese patients in spite of their genetic inheritance is needed.

The ob/ob mouse is a model of obesity and diabetes that is known to carry an autosomal recessive trait linked to a mutation in the sixth chromosome. Recently, Yiying Zhang and co-workers published the positional cloning of the mouse gene linked with this condition. Yiying Zhang et al. Nature 372: 425–32 (1994). This report disclosed a gene coding for a 167 amino acid protein with a 21 amino acid signal peptide that is exclusively expressed in adipose tissue.

Most recently, biologically active anti-obesity proteins are disclosed and claimed in Basinski et al., U.S. application Ser. No. 08/383,638, filed Feb. 6, 1995. These proteins are disclosed in SEQ ID NO: 1. The present invention provides a process for preparing an anti-obesity protein of SEQ ID NO: 1 using dipeptidyl-aminopeptidase isolated from the slime mold, Dictyostelium discoideum.

Dictyostelium discoideum is a primitive eukaryotic microorganism commonly called a slime mold, or more specifically, a cellular slime mold. The organism is found naturally on the surface of soil and dung. The wild type amoeba obtains nutrients exclusively by ingestion (phagocytosis) of whole bacteria; for this reason they are sometimes referred to as carnivorous. Axenic mutants of D. discoideum have been isolated that are capable of growth without coculture of "food" bacteria and therefore can be grown on soluble media.

Dipeptidylaminopeptidases (DAP) are enzymes that hydrolyze the penultimate amino terminal peptide bond releasing dipeptides from the unblocked amino-termini of peptides and proteins. There are currently four classes of dipeptidyl-aminopeptidases (designated DAP-I, DAP-II, DAP-III and DAP-IV) which are distinguished based on their physical characteristics and the rates at which they catalyze cleavage with various amino-terminal peptide sequences. DAP I is a relatively non-specific DAP that will catalyze the release of many dipeptide combinations from the unblocked amino termini of peptides and proteins. DAP I shows little or no activity if the emergent dipeptide is X-Pro, Arg-X, or Lys-X (where X is any amino acid). DAP II shows a preference for amino terminal dipeptide sequences that begin with Arg-X or Lys-X, and to a lesser extent, X-Pro. DAP-II exhibits significantly lower cleavage rates versus most other dipeptide combinations. DAP III appears to have a propensity toward amino terminal dipeptide sequences of the form Arg-Arg and Lys-Lys. DAP IV shows its highest rate of hydrolytic activity toward dipeptide sequences of the form X-Pro. The DAP enzymes, particularly DAP-I and DAP-IV, have been shown to be useful in processing proteins.

The present process employs yet another form of DAP, dDAP isolated from the cellular slime mold, *Dictyostelium discoideum*. Using dDAP, the anti-obesity proteins of SEQ ID NO: 1 may be prepared in high yield.

SUMMARY OF THE INVENTION

The present invention provides a process for preparing a protein of SEQ ID NO: 1, which comprises contacting the protein of SEQ ID NO: 2 with dDAP.

DETAILED DESCRIPTION OF THE INVENTION

For purposes of the present invention, as disclosed and claimed herein, the following terms and abbreviations are as defined below.

dDAP—a dipeptidylaminopeptidase, isolated from *Dictyostelium discoideum*, which demonstrates a pH optimum of about pH 3.5 with GFpNA as a substrate and has a native molecular weight of about 225,000 daltons, as measured by analytical ultracentrifugation, and a subunit molecular weight of about 66,000 daltons, as measured by SDS polyacrylamide gel electrophoresis.

Support surface—any solid or semi-solid surface or matrix that can be used as is or easily derivatized or activated to bond a protein, exhibits minimal non-specific adsorption, is physically mechanically and chemically stable, is highly porous to provide ligand accessibility, and can be regenerated without deteriorating the surface.

dDAP bed—any amount of dDAP immobilized to a single or multiple support surface that forms an aggregate volume or unit of immobilized dDAP.

GFpNA—Gly-Phe p-nitroanilide.

SEQ ID NO: 1 refers to the sequence set forth in the sequence listing and means an anti-obesity protein of the formula:

```
 1                5               10               15
Val Pro Ile Xaa Lys Val Xaa Asp Asp Thr Lys Thr Leu Ile Lys
```

```
                    20              25                30
Thr Ile Val Thr Arg Ile Xaa Asp Ile Ser His Xaa Xaa Ser Val
            35              40              45
Ser Ser Lys Xaa Lys Val Thr Gly Leu Asp Phe Ile Pro Gly Leu
            50              55              60
His Pro Ile Leu Thr Leu Ser Lys Xaa Asp Xaa Thr Leu Ala Val
            65              70              75
Tyr Xaa Xaa Ile Leu Thr Ser Xaa Pro Ser Arg Xaa Val Ile Xaa
            80              85              90
Ile Ser Xaa Asp Leu Glu Xaa Leu Arg Asp Leu Leu His Val Leu
            95              100             105
Ala Phe Ser Lys Ser Cys His Leu Pro Xaa Ala Ser Gly Leu Glu
            110             115             120
Thr Leu Xaa Ser Leu Gly Gly Val Leu Glu Ala Ser Gly Tyr Ser
            125             130             135
Thr Glu Val Val Ala Leu Ser Arg Leu Xaa Gly Ser Leu Xaa Asp
            140             145
Xaa Leu Xaa Xaa Leu Asp Leu Ser Pro Gly Cys
``` wherein:

Xaa at position 4 is Gln or Glu;

Xaa at position 7 is Gln or Glu;

Xaa at position 22 is Gln, Asn, or Asp;

Xaa at position 27 is Thr or Ala;

Xaa at position 28 is Gln, Glu, or absent;

Xaa at position 34 is Gln or Glu;

Xaa at position 54 is Met, methionine sulfoxide, Leu, Ile, Val, Ala, or Gly;

Xaa at position 56 is Gln or Glu;

Xaa at position 62 is Gln or Glu;

Xaa at position 63 is Gln or Glu;

Xaa at position 68 is Met, methionine sulfoxide, Leu, Ile, Val, Ala, or Gly;

Xaa at position 72 is Gln, Asn, or Asp;

Xaa at position 75 is Gln or Glu;

Xaa at position 78 is Gln, Asn, or Asp;

Xaa at position 82 is Gln, Asn, or Asp;

Xaa at position 100 is Gln, Trp, Tyr, Phe, Ile, Val, or Leu;

Xaa at position 108 is Asp or Glu;

Xaa at position 130 is Gln or Glu;

Xaa at position 134 is Gln or Glu;

Xaa at position 136 is Met, methionine sulfoxide, Leu, Ile, Val, Ala, or Gly;

Xaa at position 138 is Gln, Trp, Tyr, Phe, Ile, Val, or Leu; and

Xaa at position 139 is Gln or Glu.

SEQ ID NO: 2 refers to the sequence set forth in the sequence listing and means an anti-obesity protein of the formula:

```
1               5               10              15
Met Xaa Val Pro Ile Xaa Lys Val Xaa Asp Asp Thr Lys Thr Leu
            20              25              30
Ile Lys Thr Ile Val Thr Arg Ile Xaa Asp Ile Ser His Xaa Xaa
            35              40              45
Ser Val Ser Ser Lys Xaa Lys Val Thr Gly Leu Asp Phe Ile Pro
            50              55              60
Gly Leu His Pro Ile Leu Thr Leu Ser Lys Xaa Asp Xaa Thr Leu
            65              70              75
Ala Val Tyr Xaa Xaa Ile Leu Thr Ser Xaa Pro Ser Arg Xaa Val
            80              85              90
Ile Xaa Ile Ser Xaa Asp Leu Glu Xaa Leu Arg Asp Leu Leu His
            95              100             105
Val Leu Ala Phe Ser Lys Ser Cys His Leu Pro Xaa Ala Ser Gly
            110             115             120
Leu Glu Thr Leu Xaa Ser Leu Gly Gly Val Leu Glu Ala Ser Gly
            125             130             135
Tyr Ser Thr Glu Val Val Ala Leu Ser Arg Leu Xaa Gly Ser Leu
            140             145
Xaa Asp Xaa Leu Xaa Xaa Leu Asp Leu Ser Pro Gly Cys
``` wherein:

Xaa at position 2 is any amino acid except Pro;

Xaa at position 6 is Gln or Glu;

Xaa at position 9 is Gln or Glu;

Xaa at position 24 is Gln, Asn, or Asp;

Xaa at position 29 is Thr or Ala;

Xaa at position 30 is Gln, Glu, or absent;

Xaa at position 36 is Gln or Glu;

Xaa at position 56 is Met, methionine sulfoxide, Leu, Ile, Val, Ala, or Gly;

Xaa at position 58 is Gln or Glu;

Xaa at position 64 is Gln or Glu;

Xaa at position 65 is Gln or Glu;

Xaa at position 70 is Met, methionine sulfoxide, Leu, Ile, Val, Ala, or Gly;

Xaa at position 74 is Gln, Asn, or Asp;

Xaa at position 77 is Gln or Glu;

Xaa at position 80 is Gln, Asn, or Asp;

Xaa at position 84 is Gln, Asn, or Asp;

Xaa at position 102 is Gln, Trp, Tyr, Phe, Ile, Val, or Leu;

Xaa at position 110 is Asp or Glu;

Xaa at position 132 is Gln or Glu;

Xaa at position 136 is Gln or Glu;

Xaa at position 138 is Met, methionine sulfoxide, Leu, Ile, Val, Ala, or Gly;

Xaa at position 140 is Gln, Trp, Tyr, Phe, Ile, Val, or Leu; and

Xaa at position 141 is Gln or Glu.

All amino acid abbreviations used in this disclosure are those accepted by the United States: Patent and Trademark Office as set forth in 37 C.F.R. §1,822(b)(2) (1990).

As previously stated the present invention provides a process for preparing a protein of SEQ ID NO: 1, which comprises contacting the protein of SEQ ID NO: 2 with dDAP under conditions sufficient to allow the action of said dDAP to remove an amino-terminal dipeptide.

Preferred embodiments include a protein of SEQ ID NO: 2 wherein Xaa at position 2 is Arg, Asp, or Tyr. Other preferred proteins include proteins of SEQ ID NO: 2 wherein:

Xaa at position 6 is Gln;

Xaa at position 9 is Gln;

Xaa at position 24 is Asn or Asp;

Xaa at position 29 is Thr or Ala;

Xaa at position 30 is Gln or absent;

Xaa at position 36 is Gln;

Xaa at position 56 is Met;
Xaa at position 58 is Gln;
Xaa at position 64 is Gln;
Xaa at position 65 is Gln;
Xaa at position 70 is Met;
Xaa at position 74 is Asn;
Xaa at position 77 is Gln;
Xaa at position 80 is Asn;
Xaa at position 84 is Asn;
Xaa at position 102 is Trp;
Xaa at position 110 is Asp;
Xaa at position 132 is Gln;
Xaa at position 136 is Gln;
Xaa at position 138 is Met;
Xaa at position 140 is Trp; and
Xaa at position 141 is Gln.

The dDAP enzyme of the present invention is useful for converting a protein of SEQ ID NO: 2 to a protein of SEQ ID NO: 1. In any enzymatic reaction, it is critical that the cleavage site be available for the reaction to proceed. Most unexpectedly, the N-terminal of the anti-obesity proteins of SEQ ID NO: 2 are particularly suseptable to enzymatic cleavage. Thus, the present process produces a protein of SEQ ID NO: 1 in yields in excess of 90%, typically 90–95%.

Furthermore, the use of the dDAP enzyme to remove dipeptides from the anti-obesity protein is advantageous in that dDAP has a pH optimum of about 2.8, which allows the reaction to be run at acidic pH ranges. The advantages of an acidic pH reaction are recognized in the art and include lower levels of interchain disulfide dimers or polymers of the substrate are produced and oxidation of methionine residues is minimized.

An additional advantage of the present process is economical. It is more cost effective to use an enzyme from a fermentation culture, rather than to rely upon the commercial production of enzymes from animal sources, as fermentation technology allows for greater product consistency and enzyme reproducibility. The avoidance of animal-derived enzymes allows for a constant source of highly-purified bulk material. Fermentation of *D. discoideum* A×3 (ATCC 28368) followed by centrifugation, anion exchange chromatography, hydrophobic interaction chromatography and size exclusion chromatography yields a highly purified solution of dDAP enzyme which can be stored or used immediately.

The process of the present invention is accomplished at a wide variety of temperatures, pH ranges and time periods. The reaction is generally conducted in an aqueous medium suitably buffered to obtain and maintain a pH from about 2.0 to about 5.5. Preferably, the pH of the medium ranges from about 2.4 to about 4.5, and, most preferably, from about 2.4 to about 2.8. However, the skilled artisan will recognize that the pH optimum of any specific reaction will be determined by such factors as stability and solubility of the protein and enzyme. In some cases, a solubilizing agent such as urea, sodium dodecylsulfate, guanidine, and the like, may be employed.

The processing reaction can be allowed to run for any given time period, ranging from only a few seconds to several days. Preferably, the reaction is allowed to run from between about 1 minute to about 24 hours, and most preferably, from about 1 hour to about 8 hours. The skilled artisan will recognize that the time of the reaction varies with the particular conditions employed.

The temperature of the processing reaction is between about 4° C. and about 45° C. More preferably, the temperature of the reaction is between about 20° C. and about 37° C., and most preferably the reaction occurs between about 25° C. and about 37° C.

Any of a wide range of buffering agents can be employed, the only requirement being their ability to maintain a pH within the desired range. Examples of typical buffering agents are sodium phosphate, sodium acetate, sodium citrate, glycine, and the like. Preferred buffering agents are sodium acetate, sodium phosphate and glycine.

The above process may also be carried out by immobilizing dDAP onto a support surface. A solid support surfaces may include inorganic materials such as porous silica, controlled pore glass, and hydroxyapatite. Synthetic organic polymers such as polyacrylamide, polymethacrylate, and polystyrene are also illustrative support surfaces. In addition, polysaccharides such as cellulose, dextran, Sephadex®, Sepharose®, and agarose are further illustrative examples of support surfaces. Other support surfaces such as membranes and fibers are also operable. An example of a commercially available membrane is the Acti-Mod® quaternary amine module (FMC BioProducts).

Preferred support surfaces are those that do not adversely affect dDAP once bound to the surface. Commercially-available polysaccharide matrices formed into various sized beads are more preferred because they are porous, easy to handle, and are well known and understood in the biochemical purification art. More highly preferred support surfaces are commercially-available anion exchange resins. The most preferred support surface is Q Sepharose® resin (Pharmacia). See *Affinity Chromatography Principles & Methods*, Pharmacia Fine Chemicals, (1983); *Biotechnology Products Catalog* 1993, Pharmacia Biotech Inc, 800 Centennial Ave., Piscataway, N.J. 08854.

Enzyme immobilization is most usually accomplished using solid supports, generally chromatography resins, that have been modified or activated to include functional groups that permit the covalent coupling of resin to enzyme. Typically, aliphatic linker arms are employed. An example of a commercially available covalent immobilization resin is Activated CH Sepharose® 4B (Pharmacia). It is one of many types of chemistries that Pharmacia has attached to the Sepharose® 4B base matrix. In general, activated resins cost significantly more than anion exchange resins of the same base matrix, are not available in as wide of a variety of base matrix types as ion exchange chromatographic media and may therefore be more limited in their ability to handle low clarity column charges or high mobile phase flow rates.

The dDAP enzyme may also be noncovalently attached to a solid support surface, through, for example, ionic or hydrophobic mechanisms. A large variety of ion exchange and hydrophobic interaction chromatography resins are available from a large number of commercial sources, at lower cost than the activated, covalent immobilization resins.

The above discussion is in no way meant to limit the scope of the invention. The ordinarily skilled artisan will know numerous other schemes for linking proteins to support surfaces. Moreover, the choice of support surface and the method of immobilizing dDAP is largely a matter of convenience and depends on the practitioner's familiarity with, and preference for, various supports surfaces, as well as his preference for various immobilizing schemes, and knowledge of the substrate.

Once the dDAP has been immobilized onto a support surface, conversion of protein of SEQ ID NO: 2 into processed polypeptide of. SEQ ID NO: 1 can be accomplished under a variety of suitable conditions previously described. The preferred way is to pack a chromatography column with immobilized dDAP so that the substrate can be passed over the immobilized enzyme surface, allowing the reaction to proceed. Because the enzyme remains attached to the support surface, it does not become physically part of the reactant mixture and is therefore available for subsequent reuse.

The contacting step is preferably repeated one or more times to ensure complete processing of the protein. Thus, the reactant/product stream may be recycled over the same dDAP bed one or more times or may be sequentially passed over seperate dDAP beds.

The proteins of SEQ ID NO: 2 may be produced either by recombinant DNA technology or well known chemical procedures, such as solution or solid-phase peptide synthesis, or semi-synthesis in solution beginning with protein fragments coupled through conventional solution methods.

Recombinant methods are preferred if a high yield is desired. The basic steps in the recombinant production of protein include:

a) construction of a synthetic or semi-synthetic (or isolation from natural sources) DNA encoding the protein, b) integrating the coding sequence into an expression vector in a manner suitable for the expression of the protein either alone or as a fusion protein, c) transforming an appropriate eukaryotic or prokaryotic host cell with the expression vector, and d) recovering and purifying the recombinantly produced protein.

Synthetic genes, the in vitro or in vivo transcription and translation of which will result in the production of the protein may be constructed by techniques well known in the art. Owing to the natural degeneracy of the genetic code, the skilled artisan will recognize that a sizable yet definite number of DNA sequences may be constructed which encode the proteins. Techniques: for making substitutional mutations at predetermined sites in DNA having a known sequence are well known, for example M13 primer mutagenesis. The mutations that might be made in the DNA encoding the present anti-obesity proteins must not place the sequence out of reading frame and preferably will not create complementary regions that could produce secondary mRNA structure. See DeBoer et al., EP 75,444A (1983).

Methodology of synthetic gene construction is well known in the art. For example, see Brown, et al. (1979) Methods in Enzymology, Academic Press, N.Y., Vol. 68, pgs. 109–151. The DNA sequence corresponding to the synthetic protein gene may be generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404).

The gene encoding the protein may also be created by using polymerase chain reaction (PCR). The template can be a cDNA library (commercially available from CLONETECH or STRATAGENE) or mRNA isolated from human adipose tissue. Such methodologies are well known in the art Maniatis, et al. *Molecular Cloning: A Laboratory Manual,* Cold Spring Harbor Press, Cold Spring Harbor Laboratory, Cold Spring Harbor, N.Y. (1989).

Construction of suitable vectors containing the desired coding and control sequences employ standard ligation techniques. Isolated plasmids or DNA fragments are cleaved, tailored, and religated in the form desired to form the plasmids required.

To effect the translation of the desired protein, one inserts the engineered synthetic DNA sequence in any of a plethora of appropriate recombinant DNA expression vectors through the use of appropriate restriction endonucleases. A synthetic coding sequence is designed to possess restriction endonuclease cleavage sites at either end of the transcript to facilitate isolation from and integration into these expression and amplification and expression plasmids. The isolated cDNA coding sequence may be readily modified by the use of synthetic linkers to facilitate the incorporation of this sequence into the desired cloning vectors by techniques well known in the art. The particular endonucleases employed will be dictated by the restriction endonuclease cleavage pattern of the parent expression vector to be employed. The choice of restriction sites are chosen so as to properly orient the coding sequence with control sequences to achieve proper in-frame reading and expression of the protein.

In general, plasmid vectors containing promoters and control sequences that are derived from species compatible with the host cell are used with these hosts. The vector ordinarily carries a replication site as well as marker sequences which are capable of providing phenotypic selection in transformed cells. For example, *E. coli* is typically transformed using pBR322, a plasmid derived from an *E. coli* species (Bolivar, et al., *Gene:* 95 (1977)). Plasmid pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA technology.

The desired coding sequence is inserted into an expression vector in the proper orientation to be transcribed from a promoter and ribosome binding site, both of which should be functional in the host cell in which the protein is to be expressed. An example of such an expression vector is a plasmid described in Belagaje et al., U.S. Pat. No. 5,304,493, the teachings of which are herein incorporated by reference. The gene encoding A-C-B proinsulin described in U.S. Pat. No. 5,304,493 can be removed from the plasmid pRB182 with restriction enzymes NdeI and BamHI. The genes encoding the protein of the present invention can be inserted into the plasmid backbone on a NdeI/BamHI restriction fragment cassette.

In general, procaryotes are used for cloning of DNA sequences in constructing the vectors useful in the invention. For example, *E. coli* K12 strain 294 (ATCC No. 31446) is particularly useful. Other microbial strains which may be used include *E. coli* B and *E. coli* X1776 (ATCC No. 31537). These examples are illustrative rather than limiting.

Prokaryotes also are used for expression. The aforementioned strains, as well as *E. coli* W3110 (prototrophic,. ATCC No. 27325), bacilli such as Bacillus subtilis, and other enterobacteriaceae such as Salmonella typhimurium or Serratia marcescans, and various pseudomonas species may be used. Promoters suitable for use with prokaryotic hosts include the b-lactamase (vector pGX2907 [ATCC 39344] contains the replicon and b-lactamase gene) and lactose promoter systems (Chang et al., *Nature*, 275:615 (1978); and Goeddel et al., *Nature* 281:544 (1979)), alkaline phosphatase, the tryptophan (trp) promoter system (vector pATH1 [ATCC 37695] is designed to facilitate expression of an open reading frame as a trpE fusion protein under control of the trp promoter) and hybrid promoters such as the tac promoter (isolatable from plasmid pDR540 ATCC-37282). However, other functional bacterial promoters, whose nucleotide sequences are generally known, enable one of skill in the art to ligate them to DNA encoding the protein using linkers or adaptors to supply any required restriction sites.

Promoters for Use in bacterial systems also will contain a Shine-Dalgarno sequence operably linked to the DNA encoding protein.

The following preparations and examples are presented to further illustrate the present invention. The scope of the present invention is not to be construed as merely consisting of the following preparation and examples.

Preparation 1

A DNA sequence encoding the following protein sequence:

```
1              5                    10                      15
Met Arg Val Pro Ile Gln Lys Val Gln Asp Asp Thr Lys Thr Leu
               20                   25                      30
Ile Lys Thr Ile Val Thr Arg Ile Asn Asp Ile Ser His Thr Gln
               35                   40                      45
Ser Val Ser Ser Lys Gln Lys Val Thr Gly Leu Asp Phe Ile Pro
               50                   55                      60
Gly Leu His Pro Ile Leu Thr Leu Ser Lys Met Asp Gln Thr Leu
               65                   70                      75
Ala Val Tyr Gln Gln Ile Leu Thr Ser Met Pro Ser Arg Asn Val
               80                   85                      90
Ile Gln Ile Ser Asn Asp Leu Glu Asn Leu Arg Asp Leu Leu His
               95                  100                     105
Val Leu Ala Phe Ser Lys Ser Cys His Leu Pro Trp Ala Ser Gly
              110                  115                     120
Leu Glu Thr Leu Asp Ser Leu Gly Gly Val Leu Glu Ala Ser Gly
              125                  130                     135
Tyr Ser Thr Glu Val Val Ala Leu Ser Arg Leu Gln Gly Ser Leu
              140                  145
Gln Asp Met Leu Trp Gln Leu Asp Leu Ser Pro Gly Cys
``` is obtained using standard PCR methodology. A forward primer (5'-GG GG CAT ATG AGG GTA CCT ATC CAG AAA GTC CAG GAT GAC AC) and a reverse primer (5'-GG GG GGATC CTA TTA GCA CCC GGG AGA CAG GTC CAG CTG CCA CAA CAT) is used to amplify sequences from a human fat cell library (commercially available from CLONETECH). The PCR product is cloned into PCR-Script (available from STRATAGENE) and sequenced.

Preparation 2

Vector Construction

A plasmid containing the DNA sequence encoding the protein of preparation 1 is constructed to include NdeI and BamHI restriction sites. The plasmid carrying the cloned PCR product is digested with NdeI and BamHI restriction enzymes. The small~450 bp fragment is gel-purified and ligated into the vector pRB182 from which the coding sequence for A-C-B proinsulin is deleted. The ligation products are transformed into E. coli DH10B (commercially available from GIBCO-BRL) and colonies growing on tryptone-yeast (DIFCO) plates supplemented with 10 mg/mL tetracycline are analyzed. Plasmid DNA is isolated, digested with NdeI and BamHI and the resulting fragments are separated by agarose gel electrophoresis. Plasmids containing the expected~450 bp NdeI to BamHI fragment are kept. E. coli B BL21 (DE3) (commercially available from NOVOGEN) are transformed with this second plasmid expression suitable for culture for protein production.

Preparation 3

Fermentation of Dictyostelium discoideum

Lyophilized cultures of *Dictyostelium discoideum* AX3 were obtained from the American Type Culture Collection in Rockville, Md. under the accession number ATCC 28368 and were plated at several densities on agar plates (1.2% Difco Bacto Agar) containing a buffered yeast extract-peptone medium composed of (g/l): Difco Yeast Extract (7.15), Difco Bacto Peptone-(14.3), Na2HP04 (0.51) and KH2P04 (0.49), to which Glucose (10 g/l final) was added aseptically after separate sterilization and which was adjusted to a final pH of 6.5 (±0.1) with NaOH or $H_2SO_4$. This same media (without the agar) was used for liquid culture growth in volumes less than about one liter. The agar plates were incubated 3 to 5 days at 21° C. to 24° C. Spore sacks were harvested from the plate with care to prevent picking up the "food bacterium" lyophilized with the AX3 culture,, then inoculated in 3 ml of buffered yeast extract-peptone broth and incubated with gentle shaking at 21°–24° C. Thereafter, *D. discoideum* cells were amplified by serial transfer to progressively larger volumes of buffered yeast extract-peptone broth. Each serial transfer step was by a dilution between about 10- and 25-fold and occurred when cell densities exceeded about $2\times10^6$/ml. Broths were always incubated at 21°–24° C. with mild agitation.

Stirred fermentations were generally done in a similar medium with soy peptone (such as Phytone Peptone or Marcor Soy Peptone) at a concentration of 2 to 14.3 g/l substituted for the Bacto Peptone in the initial yeast extract-peptone medium. Harvests were usually from fermentors with a working volume from 10 to 5000 liters fitted with from 1 to 3 Rushton turbine impellors rotating at 40–150 RPM. Temperature was controlled at 22°±1° C., air flow controlled between 0.1 and 0.5 volumes air per volume of liquid broth and backpressure was maintained at 3–5 p.s.i. Some fermentations were done with pH controlled at 6.4 with sulfuric acid and some with dissolved oxygen controlled at 40–60% by varying agitation and air flow. Care was taken to minimize shear in handling and fermentation of the cells in that they are wall-less ameoba during growth.

In general, stirred cultures of *D. discoideum* AX3 grew with doubling times between 12 and 36 hours. Dissolved oxygen decreased progressively (when not controlled) and then began to rise some time after cell density stopped increasing. Terminal cell densities ranged between $3\times10^6$/ml and $5\times10^7$/ml, with oxygen transfer apparently limiting in those fermentations with the lower maximum cell densities.

Samples were taken occasionally and analyzed for cell density and GF-pNAse activity. A Petroff-Hauser counting chamber was used to estimate cell densities above approximately $5\times10^5$/ml. In general, GFpNA hydrolyzing activity increased throughout the fermentation. The maximum dDAP activity was seen 2 to 4 days after maximum cell density was reached. Whole broths were stored at 4° C. or frozen at −20° C. and later thawed and analyzed for activity. Fermentations were harvested by chilling to less than 10° C. and removing cells with a continuous-flow centrifuge.

Preparation 4

Preparation of dDAP

A. Cell removal and concentration

Initial purification of dDAP from *Dictyostelium discoideum* fermentation broth involves cell removal and concentration steps. Cell removal was performed by continuous-flow centrifugation on a Western States centrifuge. T,he cell free media was concentrated about 20-fold by tangential flow ultrafiltration using a 50,000 molecular weight cut-off membrane. The retentate was drained from the ultrafiltration unit and the unit was washed with 50 mM tris buffer, pH 7, to recover additional dDAP. The retentate and wash samples were combined to form a final concentrate, which was stored frozen at −20° C. for several months before further processing occurred.

B. Clarification

The frozen final concentrate was thawed for about twelve hours at room temperature. Once thawed, the final concentrate was clarified prior to the first column chromatography step. Clarification was achieved by a combination of centrifugation followed by 5 micron membrane filtration. The clarified final concentrate was adjusted to pH 7.0 and held at 4° to 10° C. for less than 12 hours while awaiting the anion exchange chromatography step.

C. Anion Exchange Chromatography

The first chromatography step of the dDAP purification process was anion exchange chromatography using Pharmacia Q-Sepharose Fast Flow resin (FFQ). The column was equilibrated with 50 mM tris buffer, pH 7. Clarified cell free concentrate was applied at 50 cm/hr linear flow rate at a ratio of 60 liters of unconcentrated fermentation media per liter of resin. This resulted in a protein charge of about 60 grams per liter resin (protein quantitation was based on the Pierce BCA Protein Assay against a standard of bovine serum albumin). About 250 units of dDAP activity were applied per liter of FFQ resin. The conductivity of the cell free concentrate was about 5 mMHOS per cm. After completing the sample charge, the FFQ resin was washed with three column volumes of equilibration buffer. The dDAP activity was eluted from the resin using a linear gradient of 0 to 1M NaCl, 50 mM tris, pH 7, applied over 10 column volumes at a flow rate of 50 cm/hr. Fraction size was 0.1 column volumes. The FFQ column was further eluted with three column volumes of 1.0M NaCl in 50 mM tris, pH 7. The effluent was monitored by conductivity and absorbance at 280 nm and fractions were assayed for dDAP activity by their ability to cleave the colorimetric substrate Gly-Phe para-nitroanilide (GFpNA) at pH 3.5. A mainstream pool was prepared by combining fractions containing about 90% of the total eluted dDAP activity. The dDAP activity eluted as a single peak about two column volumes in size. The mainstream pool was acidified to a pH of 3.5 using 10% v/v HCl. The FFQ acidified mainstream pool was held at 4° C for less than two days.

D. Hydrophobic Interaction Chromatography

The FFQ acidified mainstream pool was next purified by hydrophobic interaction chromatography (HIC) on Pharmacia Phenyl Sepharose Fast Flow resin. The column was one-third the volume of the anion exchange column. About 650 units of activity were applied per liter of resin and the protein charge was 4 grams per liter of resin (1 absorbance unit at 280 nm was equated to 1 mg/ml protein). The FFQ mainstream was prepared for charge on to the HIC column by the addition of 140 grams per liter ammonium sulfate. The charge was adjusted to pH 3.5 and the final conductivity was about 90 mMHOS per cm. The HIC column was equilibrated in 50 mM citrate, pH 3.5, containing at least 140 grams per liter ammonium sulfate. The charge was applied at a linear flow rate of 40 cm/hr and the resin was washed with at least three column volumes of equilibration buffer. The dDAP activity was eluted from the resin using a linear gradient of 140 g per liter to 0 g per liter ammonium sulfate, in 50 mM citrate, pH 3.5, applied over 10 column volumes at 40 cm/hr. The column was further eluted with at least three column volumes of 50 mM citrate, pH 3.5. Fraction size was 0.1 column volumes. The effluent was monitored by conductivity and absorbance at 280 nm and fractions were assayed for dDAP activity by their ability to cleave GFpNA at pH 3.5. A mainstream pool was prepared by combining fractions containing about 90% of the total eluted dDAP activity. The dDAP activity eluted as a single peak about two column volumes in size. The mainstream pool was adjusted to a pH of 3.5 using 10% v/v HCl or 10% w/w NaOH. The HIC mainstream was held at 4° C. for less than one day before proceeding with processing.

E. Size Exclusion Chromatography

The HIC mainstream was further processed by size exclusion chromatography (SEC) on S-200 Sepharose HR. The column was twice the volume of the HIC column and had a bed height of 78 cm. The HIC mainstream was prepared for the SEC column by concentrating the HIC mainstream in an ultrafiltration unit using a membrane with a molecular weight cut-off of 10,000 daltons. The HIC mainstream was concentrated to 2.5% the SEC column volume and the retentate drained from the unit. The ultrafiltration unit was washed with a volume of 50 mM citrate buffer, pH 3.5, equal to 2.5% the SEC column volume. The retentate and the wash were combined to form a final concentrate and adjusted to pH 3.5 with 10% v/v HCl or 10% w/v NaOH. The conductivity of the final concentrate was about 30 mMHO per cm. The SEC column was equilibrated with 50 mM acetic acid, 20 mM sodium chloride, pH 3.5, which had a conductivity of about 2 mMHO per cm. The final concentrate was applied to the SEC column at 15 cm/hr linear flow and the dDAP activity was eluted by the application of one column volume of equilibration buffer. Fraction size was 0.02 column volumes. The effluent was monitored by conductivity and absorbance at 280 nm and fractions were assayed for dDAP activity by their ability to cleave GFpNA at pH 3.5. A mainstream pool was prepared by combining fractions containing about 90% of the total eluted dDAP activity. The dDAP activity eluted as a single peak of about 0.08 column volumes in size. The SEC mainstream pool may be held at 4° C. for several months.

Purification of dDAP using a combination of anion exchange, hydrophobic interaction, and size-exclusion chromatography resulted in material that migrated as a major band on SDS-PAGE. The band migrated to a position on the gel equivalent to the molecular weight standard bovine serum albumin (66 kilodaltons). The protein was stained using ISS Pro-blue stain. The migration pattern was unaffected by the presence or absence of 0.1M DTT (plus 100° C. for 5 minutes) during sample preparation. The subunit molecular weight of DAP-I (bovine source) is estimated by SDS-PAGE to be about 22,000 daltons.

EXAMPLE 1

CONVERSION

SEQ ID NO: 3 was produced as an insoluble aggregate in the cytoplasm of E-coli. that carried a plasmid which encoded the above-mentioned protein. The insoluble protein was solubilized in 8M urea. The conversion reaction was initiated by the addition of 3–6 milliunits dDAP per mg SEQ ID NO: 3. The conversion reaction was allowed to proceed for 6–8 hours at room temperature. Reaction rates car be increased by adding more enzyme increasing the concentration of SEQ ID NO: 3 or increasing the reaction temperature. The progress of the reaction was monitored by high performance reversed phase chromatography. The reaction was terminated by adjusting the pH to 8 with NaOH. The converted des(Met-Arg)SEQ ID NO: 3 was further purified by anion exchange and size exclusion chromatography. After conversion analytical procedures including peptide mapping, N-terminal sequencing, mass spectroscopy and reversed phase HPLC indicated that the met-arg on the N-terminus was cleaved.

I claim:

1. A process for preparing a protein of SEQ ID NO: 1, which comprises contacting the protein of SEQ ID NO: 2 with dDAP; wherein dDAP is dipeptidylaminopeptidase from *Dictyostelium discoideum* having a native molecular weight of about 225,000 daltons, and a subunit molecular weight of about 66,000 daltons.

2. The process of claim 1, wherein Xaa at position 2 of SEQ ID NO: 2 is Arg.

3. The process of claim 1, wherein Xaa at position 2 of SEQ ID NO: 2 is Asp.

4. The process of claim 1, wherein Xaa at position 2 of SEQ ID NO: 2 is Tyr.

5. The process of claim 1 wherein the protein of SEQ ID NO: 2 is contacted with said dDAP between about 1 minute and about 8 hours.

6. The process of claim 5, wherein the protein of SEQ ID NO: 2 is contacted with said dDAP in a solution of between about pH 2.0 and about pH 5.5.

7. The process of claim 6, wherein the protein of SEQ ID NO: 2 is contacted with said dDAP in a solution of between about pH 2.4 and about pH 2.8.

8. The process of claim 6, wherein the protein of SEQ ID NO: 2 is contacted with said dDAP at a temperature of between about 20° C. and about 37° C.

9. The process of claim 1, wherein dDAP is immobilized on a support surface.

10. The process of claim 1 wherein the N-terminal amino acid of SEQ ID NO: 2 is an oxidized methionine.

\* \* \* \* \*